United States Patent [19]

Rizzo

[11] 4,134,913
[45] Jan. 16, 1979

[54] AMIDOSULFENYL CHLORIDE INTERMEDIATES

[75] Inventor: Victor L. Rizzo, Almena Township, Van Buren County, Mich.

[73] Assignee: The Upjohn Company, Kalamazoo, Mich.

[21] Appl. No.: 792,053

[22] Filed: Apr. 28, 1977

Related U.S. Application Data

[62] Division of Ser. No. 723,076, Sep. 14, 1976, Pat. No. 4,066,765, which is a division of Ser. No. 575,247, May 7, 1975, Pat. No. 3,998,969.

[51] Int. Cl.² .............................................. C07C 51/58
[52] U.S. Cl. ................................................. 260/543 H
[58] Field of Search .................................... 260/543 H

[56] References Cited

U.S. PATENT DOCUMENTS

| 3,699,122 | 10/1972 | Kohn | 260/543 H X |
| 3,946,062 | 3/1976 | Cleveland | 260/543 H X |

*Primary Examiner*—Gerald A. Schwartz
*Attorney, Agent, or Firm*—John J. Killinger; Sidney B. Williams, Jr.

[57] ABSTRACT

Novel pesticidal compounds of the formula:

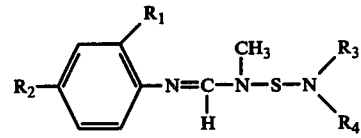

wherein $R_1$ is lower alkyl of from 1 to 4 carbon atoms; $R_2$ is hydrogen, halogen or lower alkyl of from 1 to 4 carbon atoms; $R_3$ and $R_4$ are the same or different and are hydrogen, alkyl of 1 to 8 carbon atoms, inclusive; haloalkyl, arylalkyl and

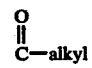

wherein alkyl is from 1 to 4 carbon atoms, cycloalkyl of from 3 to 6 carbon atoms, aryl and $R_3$ and $R_4$ taken together are a member selected from the group piperidine, morpholine, pyrazole, tribromopyrazole, N-methylpiperazine, pyrrole, pyrrolidine, pyrrolidone.

The compounds are combined with carriers to prepare compositions and are useful in controlling insect pests either as an insecticide or behavioral modifier and are particularly effective as miticides.

1 Claim, No Drawings

AMIDOSULFENYL CHLORIDE INTERMEDIATES

CROSS REFERENCE TO RELATED APPLICATIONS

This application is a divisional of application Ser. No. 723,976, filed Sept. 14, 1976, now U.S. Pat. No. 4,066,765, which is a divisional of application Ser. No. 575,247, filed May 7, 1975, which is now U.S. Pat. No. 3,998,969.

The starting materials of the compounds are evidenced in U.S. patent application Ser. No. 366,999, filed June 1, 1973, now U.S. Pat. No. 3,887,619.

BRIEF SUMMARY OF THE INVENTION

Novel compounds of the Formula I, useful as insecticides or insect behavioral modifiers. Compositions comprising a compound of the Formula I with a carrier and a method for reducing the population of undesirable insect pests.

DETAILED DESCRIPTION OF THE INVENTION

The compounds of the formula:

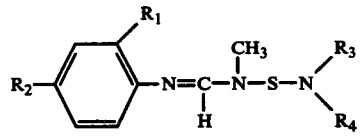

Formula I wherein $R_1$ is lower alkyl of from 1 to 4 carbon atoms; $R_2$ is hydrogen, halogen or lower alkyl of from 1 to 4 carbon atoms; $R_3$ and $R_4$ are the same or different and are hydrogen, alkyl of 1 to 8 carbon atoms; haloalkyl, arylalkyl and

wherein alkyl is from 1 to 4 carbon atoms, cycloalkyl of from 3 to 6 carbon atoms, aryl and $R_3$ and $R_4$ taken together are a member selected from the group piperidine, morpholine, pyrazole, tribromopyrazole, N-methylpiperazine, pyrrole, pyrrolidine, pyrrolidone, are prepared by reacting a compound of the formula:

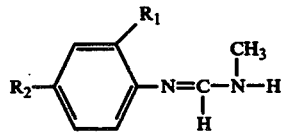

Formula II wherein $R_1$ and $R_2$ are as defined above with an amidosulfenyl chloride of the formula:

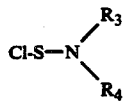

Formula III wherein $R_3$ and $R_4$ are as defined above.

The starting materials of the Formula II are disclosed in copending application Serial No. 366,999, filed June 1, 1973, now allowed. The amidosulfenyl chlorides of the Formula III are known and can be prepared, for example as disclosed in German Pat. No. 1,131,222, issued June 14, 1962.

An alternative procedure is the reaction of a mineral acid salt of a compound of Formula II with sulfur dichloride in the presence of acid acceptor compounds as defined hereafter to form a compound of the formula:

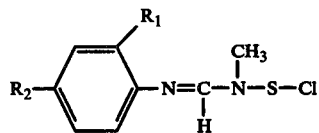

Formula IV and then reacting with an amine of the formula:

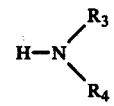

wherein $R_3$ and $R_4$ are as defined above under reaction conditions previously described.

The compounds of Formula IV are novel intermediates used in this alternative procedure, and their preparations are indicated below:

Preparation 1 —
Methyl-(N-2,4-xylylformamidoyl)amidosulfenyl Chloride

To a solution of 19.8 g. (0.1 mole) of N-methyl-N-2,4-xylylformamidine hydrochloride in 250 ml. of methylene chloride is added 20.2 g. (0.2 mole) of triethylamine. The reaction mixture is cooled to −10° C. and a solution of 10.3 g. (0.1 mole) sulfur dichloride in 10 ml. methylene dichloride is added dropwise keeping the temperature below 0° C. After addition the reaction mixture is allowed to warm to 15° C. About two-thirds of the methylene dichloride is removed on a rotary evaporator and 250 ml. of hexane added. The remainder of the methylene dichloride is removed and an additional 250 ml. of hexane added. At this point the sulfenyl chloride and suspension of triethylamine hydrochloride are ready to be reacted with an appropriate amino compound.

Preparation 2 —
Methyl-[N-(4-chloro-2-methylphenyl)formimidoyl-]amidosulfenyl chloride Following the procedure of preparation 1, but substituting N-methyl-N'-(4-chloro-2-methylphenyl)formamidine hydrochloride for N-methyl-N'-2,4-xylylformamidine hydrochloride, the desired sulfenyl compound is obtained.

The above described reactions are advantageously carried out in the presence of an inert organic solvent. An inert organic solvent is defined herein as a solvent for the formamidine reactant (II) which does not enter into reaction with the reaction mixture components or in any way alter the desired course of the reaction. Illustrative of inert organic solvents are tetrahydrofuran, benzene, diethylether, and methylene chloride. Preferred as the inert organic solvent is tetrahydrofuran.

The proportion of solvent employed is not critical, but advantageously is a sufficient quantity to solubilize the reactant formamidine (II).

During the course of the above illustrated reaction, hydrochloric acid is generated as a by-product. Preferably this acid is removed from the reaction mixture as it forms. This may be accomplished by conventional and known methods, for example by adding an acid acceptor compound to the reaction mixture. Examples of acid acceptor compounds are the tertiary amines such as trimethylamine, triethylamine, tripropylamine, tributylamine, pyridine and the like.

Although the above reaction may be carried out over a broad range of temperature conditions, i.e., from about −30° C. to about reflux temperature for the reaction mixture, it is preferably carried out at about 0° C.

Progress of the above reaction may be followed by conventional analytical methods, such as for example by nuclear magnetic resonance analysis which will show spectral characteristics of the product compounds (I) or by thin-layer chromatography which will show the appearance of product compounds (I). Upon completion of the reaction, the desired compounds (I) are readily separated from the reaction mixture by conventional methods such as by filtration to remove solid residues and distillation to removed solvents.

The following examples are illustrative of the process and products of the present invention but are not to be construed as limiting.

EXAMPLE 1 —
N-Methyl-N-[(dimethylamino)thio]-N'-2,4-xylylformamidine

To 14.6 g. (0.09 mole) N-methyl-N'-2,4-xylylformamidine in 250 ml. tetrahydrofuran is added 9.09 g. (0.09 mole) triethylamine. The reaction mixture is cooled to 10° C. in an ice bath and 10.05 g. (0.09 mole) dimethylaminosulfenyl chloride is added to the stirred solution. The reaction mixture is stirred at room temperature for ½ hour, the solid filtered off, and the solvent removed. The product is filtered through a sintered glass filter to remove traces of solid impurity. A yield of 19.2 g. (90.0%) of an amber oil is obtained. The NMR and TLC were reasonable for the desired product.

Analysis: Calc'd. for $C_{12}H_{19}N_3S$: C, 60.72; H, 8.07; N, 17.70. Found: C, 60.96; H, 8.20; N, 17.55.

EXAMPLE 2
N-Methyl-N-[(dimethylamino)thio]-N'-(2-methyl-4-chlorophenyl)formamidine To 10.9 g. (0.06 mole) N-methyl-N'-(2-methyl-4-chlorophenyl)formamidine in 150 ml. of tetrahydrofuran is added 6.06 g. (0.06 mole) triethylamine. The reaction mixture is cooled to 10° C. in an ice bath and 6.7 g. (0.06 mole) dimethylamidosulfenyl chloride is added to the stirred solution. The reaction mixture is stirred at room temperature for ½ hour. The solid is filtered off and the solvent removed. The residue is taken up in 200 ml. of hexane and extracted with 0.02 moles HCl in 200 ml. of water. The hexane layer is dried over $MgSO_4$, filtered, and the solvent removed to yield 7.6 g. (49%) of an amber oil. The NMR and TLC were reasonable for the desired product.

Analysis: Calc'd. for $C_{11}H_{16}ClN_3S$: C, 51.25; H, 6.26; N, 16.30. Found: C, 51.40; H, 6.23; N, 15.89.

EXAMPLE 3 —
N-Methyl-N-[(diphenylamino)thio]-N'-(2-methyl-4-chlorophenyl)formamidine To 16.9 g. (0.1 mole) diphenylamine and 10.1 g. (0.1 mole) triethylamine in 250 ml. tetrahydrofuran is added a solution of N-methyl-N'-(2-methyl-4-chlorophenyl)-formamidine-N-sulfenyl chloride (0.1 mole) in tetrahydrofuran keeping the temperature below 25° C. with slight cooling. Stirred 10 minutes at room temperature, filtered, and removed solvent. The residue is taken up in hexane and washed with a solution of 8 g. citric acid in 250 ml. of water. The hexane layer is dried and the solvent removed. The product is recrystallized from ether at −40° C. to obtain 12.2 g. (32% yield), m.p. 78°–79° C.

Analysis: Calc'd. for $C_{21}H_{20}ClN_3S$: C, 66.04; H, 5.28; N, 11.00. Found: C, 65.93; H, 5.20; N, 10.92.

EXAMPLE 4 —
N-Methyl-N-(N-methylpiperazinothio)-N'-2,4-xylylformamidine

To 10.0 g. (0.10 moles) N-methylpiperazine in 250 ml. of hexane is added a solution of 0.05 moles N-methyl-N'-2,4-xylylformamidine-N-sulfenyl chloride in hexane with slight cooling. The reaction mixture is stirred for ½ hour and the solid filtered off. The hexane solution is extracted with 0.02 moles HCl in 200 ml. water. The hexane solution is dried and the solvent removed to obtain an amber oil. The NMR is reasonable for the desired product.

EXAMPLE 5 —
N-Methyl-N-[(N-methylcyclohexylamino)thio]-N'-(2-methyl-4-chlorophenyl)formamidine To 11.3 g. (0.10 mole) of N-methylcyclohexylamine in 250 ml of hexane is added a solution of 0.05 moles of N-methyl-N'-(2-methyl-4-chlorophenyl)formamidine-N-sulfenyl chloride in hexane with slight cooling. The reaction mixture is filtered and the hexane solution extracted with 0.02 moles HCl in 200 ml. of water. The hexane solution is dried and the solvent removed to obtain an amber oil. The NMR is reasonable for the desired product.

EXAMPLE 6 —
N-Methyl-N-[(dicyclohexylamino)thio]-N'-2,4-xylylformamidine

To 18.6 g. (0.103 mole) of dicyclohexylamine in 250 ml. of hexane is added a solution of 0.05 moles of N-methyl-N'-2,4-xylylformamidine-N-sulfenyl chloride in hexane with slight cooling. The reaction mixture is stirred for ½ hour and the solid filtered off. The solvent is removed and the solid that is obtained is triturated with 10 ml. of cold Skellysolve F and recrystallized from Skellysolve F to obtain 2.7 g. of white crystalline product having a melting point of 97°–98° C.

Analysis: Calc'd. for $C_{22}H_{35}N_3S$: C, 70.73; H, 9.44; N, 11.25. Found: C, 70.96; H, 9.64; N, 11.43.

EXAMPLE 7 —
N-Methyl-N-[(dicyclohexylamino)thio]-N'-(2-methyl-4-chlorophenyl)formamidine To 18.6 g. (0.103 mole) of dicyclohexylamine in 250 ml. of hexane is added a solution of 0.05 moles of N-methyl-N'-(2-methyl-4-chlorophenyl)formamidine-N-sulfenyl chloride in hexane with slight cooling. The reaction mixture is stirred for ½ hour and the solid filtered off. The solvent is removed and the solid that is obtained is triturated with 10 ml. of cold Skellysolve F and then recrystallized from Skellysolve B to obtain 1.9 g. of white crystalline product having a melting point of 110°–111° C.

Analysis: Calc'd. for $C_{21}H_{32}ClN_3S$: C, 64.01; H, 8.19; N, 10.66. Found: C, 64.23; H, 8.68; N, 10.65.

EXAMPLE 8 —
N-Methyl-N-[(dibenzylamino)thio]-N'-(2-methyl-4-chlorophenyl)formamidine To 19.7 g. (0.10 moles) of dibenzylamine in 300 ml. of hexane is added a solution of 0.05 moles N-methyl-N'-(2-methyl-4-chlorophenyl)formamidine-N-sulfenyl chloride in 400 ml. of hexane with slight cooling. The reaction mixture is stirred for 1½ hours, and the solid filtered off. The solvent is removed and the residue recrystallized from Skellysolve B to obtain 8.0 g. (39% yield) of a white solid, m.p. 97°–99° C.

Analysis: Calc'd. for $C_{23}H_{24}ClN_3S$: C, 67.38; H, 5.90; N, 10.25. Found: C, 67.49; H, 6.14; N, 10.12.

EXAMPLE 9 —
N-Methyl-N-[(diethylamino)thio]-N'-2,4-xylylformamidine

Following the procedure of Example 2, but substituting diethylamidosulfenyl chloride for dimethylamidosulfenyl chloride the product is obtained as an amber oil; 7.2 g. (90.5% yield). The NMR is reasonable for the desired product.

Analysis: Calc'd. for $C_{14}H_{23}N_3S$: C, 63.36; H, 8.73; N, 15.83. Found: C, 63.44; H, 8.62; N, 15.85.

EXAMPLE 10 —
N-Methyl-N-[(di-n-propylamino)thio]-N'-2,4-xylylformamidine

Following the procedure of Example 2, but substituting di-n-propylamidosulfenyl chloride for dimethylamidosulfenyl chloride the product is obtained as an amber oil; 7.7 g. (87.5% yield). The NMR is reasonable for the desired product.

Analysis: Calc'd. for $C_{16}H_{27}N_3S$: C, 65.48; H, 9.27; N, 14.32. Found: C, 65.18; H, 9.24; N, 14.32.

EXAMPLE 11 —
N-Methyl-N-[(diisopropylamino)thio]-N'-2,4-xylylformamidine

Following the procedure of Example 2, but substituting diisopropylamidosulfenyl chloride for dimethylamidosulfenyl chloride, the product is obtained as an amber oil; 7.2 g. (82.5% yield). The NMR is reasonable for the desired product.

Analysis: Calc'd. for $C_{16}H_{27}N_3S$: C, 65.48; H, 9.27; N, 14.32. Found: C, 65.90; H, 9.34; N, 14.34.

EXAMPLE 12 —
N-Methyl-N-[(di-n-butylamino)thio]-N'-2,4-xylylformamidine

Following the procedure of Example 2, but substituting di-n-butylamidosulfenyl chloride for dimethylamidosulfenyl chloride, the product is obtained as an amber oil; 8.0 g (83.5% yield). The NMR is reasonable for the desired product.

Analysis: Calc'd. for $C_{18}H_{31}N_3S$: C, 67.24; H, 9.72; N, 13.07. Found: C, 67.01; H, 9.58; N, 12.87.

EXAMPLE 13 —
N-Methyl-N-(morpholinothio)-N'-2,4-xylylformamidine

Following the procedure of Example 2, but substituting morpholinosulfenyl chloride for dimethylamidosulfenyl chloride the product is obtained as an amber oil; 25 g. (90.0% yield). The NMR is reasonable for the desired product.

Analysis: Calc'd. for $C_{14}H_{21}N_3OS$: C, 60.18; H, 7.54; N, 15.04. Found: C, 59.87; H, 7.41; N, 15.06.

EXAMPLE 14 —
N-Methyl-N-(piperidinothio)-N'-2,4-xylylformamidine

Following the procedure of Example 2, but substituting piperidinosulfenyl chloride for dimethylamidosulfenyl chloride, the product is obtained as an amber oil; 5.8 g. (70.0% yield). The NMR is reasonable for the desired product.

Analsysis: Calc'd. for $C_{15}H_{23}N_3S$: C, 64.94; H, 8.36; N, 15.15. Found: C, 64.97; H, 8.18; N, 15.12.

EXAMPLE 15 —
N-Methyl-N-[(ethyl-n-butylamino)thio]-N'-2,4-xylylformamidine

Following the procedure of Example 2, but substituting N-ethyl-N-n-butylamidosulfenyl chloride for dimethylamidosulfenyl chloride the product is obtained as an amber oil; 6.6 g. (71.5% yield).

Analysis: Calc'd. for $C_{16}H_{27}N_3S$: C. 65.48; H, 9.27; N, 14.32. Found: C, 65.64; H, 9.29; N, 14.23.

EXAMPLE 16 —
N-Methyl-N-[(diisobutylamino)thio]-N'-2,4-xylylformamidine

Following the procedure of Example 2, but substituting diisobutylamidosulfenyl chloride for dimethylamidosulfenyl chloride, the product is obtained as an amber oil; 8.3 g. (86.5% yield). The NMR is reasonable for the desired product.

Analysis: Calc'd. for $C_{18}H_{31}N_3S$: C, 67.24; H, 9.72; N, 13.07. Found: C, 67.40; H, 9.29; N, 13.00.

EXAMPLE 17 —
N-Methyl-N-[(methyl-n-butylamino)thio]-N'-2,4-xylylformamidine

Following the procedure of Example 2, but substituting N-methyl-N-n-butylamidosulfenyl chloride for dimethylamidosulfenyl chloride, the product is obtained as an amber oil; 7.8 g. (86.0% yield). The NMR is reasonable for the desired product.

Analysis: Calc'd. for $C_{15}H_{25}N_3S$: C, 64.47; H, 9.02; N, 15.04. Found: C, 63.98; H, 9.17; N, 14.34.

EXAMPLE 18 —
N-Methyl-N-[(methyl-n-butylamino)thio]-N'-(2-methyl-4-chlorophenyl)formamidine Following the procedure of Example 2, but substituting N-methyl-N-n-butylamidosulfenyl chloride for dimethylamidosulfenyl chloride, the product is obtained as an amber oil; 7.8 g. (79.0% yield). The NMR is reasonable for the desired product.

Analysis: Calc'd for $C_{14}H_{22}N_3SCl$: N, 13.70. Found: N, 14.01.

EXAMPLE 19 —
N-Methyl-N-[(diethylamino)thio]-N'-(2-methyl-4-chlorophenyl)formamidine Following the procedure of Example 2, but substituting diethylamidosulfenyl chloride for dimethylamidosulfenyl chloride, the product is obtained as an amber oil; 7.8 g. (91.5% yield). The NMR is reasonable for the desired product.

Analysis: Calc'd. for $C_{13}H_{20}N_3SCl$: C, 54.61; H, 7.05; N, 14.70. Found: C, 54.57; H, 6.90; N, 14.73.

EXAMPLE 20 —
N-Methyl-N-[(di-n-propylamino)thio]-N'-(2-methyl-4-chlorophenyl)formamidine Following the procedure of Example 2, but substituting di-n-propylamidosulfenyl chloride for dimethylamidosulfenyl chloride, the product is obtained as an amber oil; 7.7 g. (82.0% yield). The NMR is reasonable for the desired product.

Analysis: Calc'd. for $C_{15}H_{24}N_3SCl$: C, 57.40; H, 7.71; N, 13.39. Found: C, 57.71; H, 7.51; N, 13.12.

EXAMPLE 21 —
N-Methyl-N-[(diisopropylamino)thio]-N'-(2-methyl-4-chlorophenyl)formamidine Following the procedure of Example 2, but substituting diisopropylamidosulfenyl chloride for dimethylamidosulfenyl chloride, the product is obtained as an amber oil; 8.0 g. (85.0% yield). The NMR is reasonable for the desired product.

Analysis: Calc'd. for $C_{15}H_{24}N_3SCl$: C, 57.40; H, 7.71; N, 13.39. Found: C, 57.44; H, 7.67; N, 13.48.

EXAMPLE 22 —
N-Methyl-N-[(di-n-butylamino)thio]-N'-(2-methyl-4-chlorophenyl)formamidine Following the procedure of Example 2, but substituting di-n-butylamidosulfenyl chloride for dimethylamidosulfenyl chloride, the product is obtained as an amber oil; 8.4 g. (81.5% yield). The NMR is reasonable for the desired product.

Analysis: Calc'd. for $C_{17}H_{28}N_3SCl$: C, 59.72; H, 8.25; N, 12.29. Found: C, 59.58; H, 8.55; N, 12.19.

EXAMPLE 23 —
N-Methyl-N-(piperidinothio)-N'-(2-methyl-4-chlorophenyl)formamidine Following the procedure of Example 2, but substituting piperidinosulfenyl chloride for dimethylamidosulfenyl chloride, the product is obtained as an amber oil; 7.0 g. (78.0% yield). The NMR is reasonable for the desired product.

Analysis: Calc'd. for $C_{14}H_{20}N_3SCl$: C, 56.46; H, 6.77; N, 14.11. Found: C, 56.34; H, 6.95; N, 13.91.

EXAMPLE 24 —
N-Methyl-N-[(ethyl-n-butylamino)thio]-N'-(2-methyl-4-chlorophenyl)formamidine Following the procedure of Example 2, but substituting N-ethyl-N-n-butylamidosulfenyl chloride for dimethylamidosulfenyl chloride, the product is obtained as an amber oil; 8.1 g. (87.0% yield). The NMR is reasonable for the desired product.

Analysis: Calc'd. for $C_{15}H_{24}N_3SCl$: C, 57.40; H, 7.71; N, 13.39. Found: C, 57.25; H, 7.56; N, 13.41.

EXAMPLE 25 —
N-Methyl-N-[(diisobutylamino)thio]-N'-(2-methyl-4-chlorophenyl)formamidine Following the procedure of Example 2, but substituting diisobutylamidosulfenyl chloride for dimethylamidosulfenyl chloride, the product is obtained as an amber oil; 9.0 g. (88.3% yield). The NMR is reasonable for the desired product.

Analysis: Calc'd. for $C_{17}H_{28}N_3SCl$: C, 59.72; H, 8.25; N, 12.29. Found: C, 59.88; H, 8.11; N, 12.27.

EXAMPLE 26 —
N-Methyl-N-[($\beta,\beta'$-dichlorodiethylamino)thio]-N'-(2-methyl-4-chlorophenyl)formamidine Following the procedure of Example 2, but substituting $\beta,\beta'$-dichlorodiethylamidosulfenyl chloride for dimethylamidosulfenyl chloride, the product is obtained as an amber oil; 7.5 g. (84.0% yield). The NMR is reasonable for the desired product.

Analysis: Calc'd. for $C_{13}H_{18}N_3SCl_3$: C, 44.02; H, 5.11; N, 11.85. Found: C, 44.18; H, 5.29; N, 12.02.

EXAMPLE 27 —
N-Methyl-N-[(diethylamino)thio]-N'-(2-methyl-4-bromophenyl)formamidine Following the procedure of Example 2, but substituting diethylamidosulfenyl chloride for dimethylamidosulfenyl chloride, the product is obtained as an amber oil; 5.8 g. (88.0% yield). The NMR is reasonable for the desired product.

Analysis: Calc'd. for $C_{13}H_{20}N_3SBr$: C, 47.28; H, 6.10; N, 12.72. Found: C, 47.36; H, 6.08; N, 12.75.

EXAMPLE 28 —
N-Methyl-N-[(di-n-propylamino)thio]-N'-(2-methyl-4-bromophenyl)formamidine Following the procedure of Example 2, but substituting di-n-propylamidosulfenyl chloride for dimethylamidosulfenyl chloride, the product is obtained as an amber oil; 5.7 g. (80.0% yield). The NMR is reasonable for the desired product.

Analysis: Calc'd. for $C_{15}H_{24}N_3SBr$: C, 50.28; H, 6.75; N, 11.73. Found: C, 50.53; H, 6.80; N, 11.58.

EXAMPLE 29 —
N-Methyl-N-[(diisopropylamino)thio]-N'-(2-methyl-4-bromophenyl)formamidine Following the procedure of Example 2, but substituting diisopropylamidosulfenyl chloride for dimethylamidosulfenyl chloride, the product is obtained as an amber oil; 5.8 g. (81.0% yield). The NMR is reasonable for the desired product.

Analysis: Calc'd. for $C_{15}H_{24}N_3SBr$: C, 50.28; H, 6.75; N, 11.73. Found: C, 50.26; H, 6.75; N, 11.65.

EXAMPLE 30 —
N-Methyl-N-[(N-methylanilino)thio]-N'-2,4-xylylformamidine

Following the procedure of Example 6, but substituting tetrahydrofuran solvent for hexane, and N-methylaniline for dicyclohexylamine, the product is obtained as a white solid; 7.6 g. (25.4% yield); m.p. 72°–73.5° C. The NMR is reasonable for the desired product.

Analysis: Calc'd. for $C_{17}H_{21}N_3S$: C, 68.19; H, 7.07; N, 14.04. Found: C, 68.43; H, 7.02; N, 13.75.

EXAMPLE 31 —
N-Methyl-N-[(N-ethylanilino)thio]-N'-2,4-xylylformamidine

Following the procedure of Example 6, but substituting tetrahydrofuran solvent for hexane, and N-ethylaniline for dicyclohexylamine, the product is obtained as a white solid; 4.5 g. (29.0% yield); m.p. 52°–53° C. The NMR is reasonable for the desired product.

Analysis: Calc'd. for $C_{18}H_{23}N_3S$: C, 68.97; H, 7.39; N, 13.41. Found: C, 68.63; H, 7.40; N, 13.16.

EXAMPLE 32 —
N-Methyl-N-[(N-methylanilino)thio]-N'-(2-methyl-4-chlorophenyl)formamidine Following the procedure of Example 7, but substituting N-methylaniline for dicyclohexylamine, the product is obtained as a white solid; 4.3 g. (34.0% yield), m.p. 65°–67° C. The NMR is reasonable for the desired product.

Analysis: Calc'd. for $C_{16}H_{18}N_3SCl$: C, 60.08; H, 5.67; N, 13.14. Found: C, 60.06; H, 5.78; N, 13.07.

EXAMPLE 33 —
N-Methyl-N-[(N-ethylanilino)thio]-N'-(2-methyl-4-chlorophenyl)formamidine Following the procedure of Example 7, but substituting N-ethylaniline for dicyclohexylamine, the product is obtained as a white solid; 2.8 g. (21.0% yield); m.p. 51.5°–53° C. The NMR is reasonable for the desired product.

Analysis: Calc'd. for $C_{17}H_{20}N_3SCl$: C, 61.15; H, 6.04; N, 12.58. Found: C, 61.61; H, 6.37; N, 12.81.

EXAMPLE 34 —
N-Methyl-N-(morpholinothio)-N'-(2-methyl-4-chlorophenyl)formamidine Following the procedure of Example 7, but substituting morpholine for dicyclohexylamine, the product is obtained as an amber oil on removal of the solvent; 12.0 g. (80.0% yield). The NMR is reasonable for the desired product.

Analysis: Calc'd. for $C_{13}H_{18}N_3SOCl$: N, 14.01. Found: N, 14.02.

EXAMPLE 35 —
N-Methyl-N-[(2,2'-diphenyldiethylamino)thio]-N'-(2-methyl-4-chlorophenyl)formamidine Following the procedure of Example 8, but substituting N,N-2,2'-diphenyldiethylamine for dibenzylamine, the product can be obtained.

EXAMPLE 36 —
N-Methyl-N-[(2,2'-diphenyldipropyl)thio]-N'-(2-methyl-4-chlorophenyl)formamidine Following the procedure of Example 8, but substituting N,N-2,2'-diphenyldipropylamine for dibenzylamine, the product can be obtained.

EXAMPLE 37 —
N-Methyl-N-[(di-n-hexylamino)thio]-N'-(o-tolyl)-formamidine

Following the procedure of Example 2, but substituting N-methyl-N'-o-tolylformamidine for N-methyl-N'-(2-methyl-4-chlorophenyl)formamidine, and di-n-hexylamidosulfenyl chloride for dimethylamidosulfenyl chloride, the product can be obtained.

EXAMPLE 38 —
N-Methyl-N-[(dicyclopentylamino)thio]-N'-(2-methyl-4-bromophenyl)formamidine Following the procedure of Example 2, but substituting dicyclopentylamidosulfenyl chloride for dimethylamidosulfenyl chloride, the product can be obtained.

EXAMPLE 39 —
N-Methyl-N-[(N-n-butanol-N-ethylamino)thio]-N'-2,4-xylylformamidine Following the procedure of Example 2, but substituting N-n-butanoyl-N-ethylamidosulfenyl chloride for dimethylamidosulfenyl chloride, the product can be obtained.

EXAMPLE 40 —
N-Methyl-N-(pyrrolidinothio)-N'-2,4-xylylformamidine

Following the procedure of Example 2, but substituting pyrrolidinosulfenyl chloride for dimethylamidosulfenyl chloride, the product can be obtianed.

EXAMPLE 41 —
N-Methyl-N-(pyrazolothio)-N'-2,4-xylylformamidine

Following the procedure of Example 2, but substituting pyrazolosulfenyl chloride for dimethylamidosulfenyl chloride, the product can be obtained.

EXAMPLE 42 —
N-Methyl-N-(2-oxopyrrolidinothio)-N'-2,4-xylylformamidine

Following the procedure of Example 2, but substituting 2-oxopyrrolidinosulfenyl chloride for dimethylamidosulfenyl chloride, the product can be obtained.

EXAMPLE 43 —
N-Methyl-N-(1-pyrrolothio)-N'-2,4-xylylformamidine

Following the procedure of Example 2, but substituting N-pyrrolylsulfenyl chloride for dimethylamidosulfenyl chloride, the product can be obtained.

EXAMPLE 44 —
N-Methyl-N-[(N-cyclohexylanilino)thio]-N'-(2-methyl-4-chlorophenyl)formamidine Following the procedure of Example 2, but substituting N-cyclohexylanilinosulfenyl chloride for dimethylamidosulfenyl chloride, the product can be obtained.

The compounds of the Formula I are particularly advantageous commercially as invertebrate pesticides. For example, they are relatively stable both in storage and upon application in the field thus providing a long-lasting residual effectiveness.

In addition to killing invertebrate pests on contact, the compounds of the invention are absorbed by the vascular system of many plants, for example by cotton plants, and act systemically to kill the adult pests feeding upon the plant. Thus their period of pesticidal activity is further extended and non-feeding insects, i.e., insects not harmful to the plant are not unnecessarily killed during the whole period of pesticidal activity.

Compounds of the invention are also ovicidal, and are particularly effective in the control of acarine pest populations by this ovicidal action. Lepidopterous ova are also particularly susceptible to the compounds of the invention.

The compounds of the Formula I are also advantageous in that they exhibit relatively low mammalian toxicity and are non-phytotoxic at effective concentrations.

The invention also comprises invertebrate pesticidal compositions which comprise a pesticidally acceptable carrier and a pesticidally effective amount of a compound (I) of the invention. The compositions are useful in the method of the invention which is a process for controlling invertebrate pests, which comprises applying to a situs, effective amounts of the compounds (I) of the invention.

By the term "situs" I mean plants such as ornamentals, food crops, fruit trees, textile producing plants, berry bushes, lumber forsts, farm yards, animal shelters, buildings, sanitary land-fill areas and like sites which are infected with or are potential infestation sites for invertebrate pests controllable with the compounds (I) of the invention.

The novel compounds (I) of the invention are useful in controlling invertebrate pest populations, i.e., in killing adults are ova of invertebrate pests or animals of the Phylum Arthropoda, for example those of Class Insecta such as those of the order Coleoptera as illustrated by the cotton ball weevil (*Anthonomus grandis* Boheman); those of the order Lepidoptera as illustrated by the southern army worm (*Prodenia eridania* Cramer); those of Class Arachnida such as those of the order Acarina as illustrated by the two-spotted spider mite (*Tetranychus telarius* Linnaeus or *Tetranychus urticae* Koch).

In addition to being effective in pest control through to modality of lethal effect, the compounds are effective in control as a behavioral modifier. For example, young lepidopteran larvae, aphids and mites are repelled by the chemicals or treated foliage, resulting in a marked reduction in population density. Adult moths are repelled and refuse to ovipost on treated plant parts. In addition, adult moths undergo chronic toxicity symptoms, i.e., increased wing beating with a resultant loss of wing scales and a premature death.

The pesticidal compounds (I) may be employed to control invertebrate pest populations, in their pure forms. However, it is preferred that they be applied to a situs in the form of a composition, comprising the compound (I) and a pesticidally acceptable diluent or carrier. Pesticidally acceptable carriers or diluents are well known in the art. For example, those compounds (I) which are solids at ambient temperatures may be formulated as granulars, dusts, wettable powders, emulsifiable concentratres, aqueous dispersions, solutions, and flowable creams for application to insects, mites, objects, or a situs. Those compounds (I) which are liquids at ambient temperatures may be formulated as emulsifiable concentrates, aqueous dispersions, suspensions, solutions, aerosols and the like.

The compounds (I) of the invention may also be admixed with other known pesticides to form compositions of the invention. For example, they may be mixed with malathion, azinphosmethyl, carbaryl, methoxychlor, and like pesticidal compounds.

The compounds (I) of the invention may be applied to insects, mites, objects, or a situs in aqueous sprays without a solid carrier. Such aqueous sprays are advantageous for certain types of spray equipment and conditions of application as is well known in the art. They are also advantageous when uniform dispersions, homogeneous solutions, or other easily mixed aqueous sprays are desired.

Aqueous sprays without a solid carrier are prepared from concentrated solutions of the compounds (I) of the invention in an inert organic solvent carrier. The inert organic solvent carrier may be one that is miscible or immiscible with water. The compounds (I) that are somewhat soluble in water may be dissolved in a water miscible solvent carrier, e.g., ethanol and mixed with water to give homogeneous solutions. The compounds (I) that are less soluble in water may be dissolved in a solvent carrier that is immiscible with water and the solution dispersed in water to give a uniform dispersion, e.g., an emulsion.

In an oil-in-water emulsion, the solvent phase is dispersed in the water phase and the dispersed phase contains the compound (I). In this way, uniform distribution of a water insoluble compound (I) is achieved in an aqueous spray. A solvent carrier in which the compounds (I) are highly soluble is desirable so that relatively high concentrations of the compound (I) can be obtained. One or more solvent carriers with or without a co-solvent may be used in order to obtain concentrated solutions of the compounds (I), the main consideration being to employ a water-immiscible solvent for the compound (I) that will hold the compound in solution over the range of concentration useful for applying to invertebrate pests or a situs.

The emulsifiable concentrate compositions of the invention are preferred compositions prepared by dissolving the compound (I) as the active ingredient and a surfactant such as one of those previously described, in a substantially water-immiscible solvent carrier (i.e., a solvent carrier which is soluble in water to the extent of less than 2.5% by volume at temperatures of the order of 20° C. to 30° C.), for example, cyclohexanone, methyl propyl ketone, summer oils (a paraffinic, intermediate distillation fraction having a viscosity range from 40 to 85 seconds Saybolt and an unsulfonatable residue over 90 percent), ethylene dichloride; aromatic hydrocarbons such as benzene, toluene, and xylene, and high-boiling petroleum hydrocarbons such as kerosene, diesel oil, and the like. When desired, a co-solvent such as methyl ethyl ketone, acetone, isoproponal, and the like may be included with the solvent carrier in order to enhance the solubility of the compound (I). Aqueous emulsions are prepared by mixing the concentrte with water to give any desired concentration of compounds (I).

Advantageously, the concentration of compound (I) in emulsifiable concentrates will range from about 5 percent to about 50 percent by weight, preferably from about 10 percent to about 40 percent. A concentrate comprising 20 percent by weight of the compound (I) dissolved in a waterimmiscible solvent of the kind noted above may be admixed with an aqueous medium in the proportions of 13 ml. of concentrate with 1 gal. of medium to give a mixture containing 700 parts of compounds (I) per million parts of liquid carrier. Similarly, 1 qt. of a 20 percent concentrate mixed with 40 gals. of water provides about 1200 ppm (parts per million) of a compound (I). In the same manner, more concentrated solutions of active ingredient may be prepared by adjusting upward the proportion of compound (I).

The above described concentrate compositions of the invention which are intended for use in the form of aqueous dispersions or emulsions may also contain advantageously a humectant, i.e., an agent which will delay the drying of the composition in contact with material to which it has been applied. Conventionally used humectants are exemplified by glycerol, diethylene glycol, solubilized lignins, such as calcium ligninsulfonate, and the like.

For use in an aerosol, the compound (I) may be dissolved in acetone or a mixture of acetone and a heavy petroleum oil and mixed in a thick-walled canister or bomb with a propellant such as methyl chloride or dichlorodifluoromethane.

The compositions containing compounds (I) of the invention may be applied to invertebrate pests or pestiferous sites by conventional methods. For example, an area of soil, a building, or plants may be treated by spraying emulsions, or solutions from hand-operated knapsack sprayers. Creams and ointment formulations may be applied to objects for prolonged protection from insects and mites.

It will of course be appreciated by those skilled in the art that the conditions encountered when applying the method and compositions of this invention to actual practice can vary widely. Among the variables that may be encountered are the degree of infestation by pests, the particular pest to be controlled, the specific compound (I) employed, the particular situs being treated, the age or degree of development of plants to be protected, the prevailing weather conditions, such as temperatures, relative humidity, rainfall, dews, and like environmental conditions. Dependent upon the variables encountered in a given situation, the amount of compounds (I) to be employed as an effective amount, the frequency of application and the technique of application will be adjusted for optimum effect, as those skilled in the art well appreciate.

In general, efficacy of the compounds (I) against invertebrate pests has been demonstrated at concentrations of 1000, 500, 100, 50 and even 30 ppm of the novel compounds (I) depending upon the specific pest to be killed. Some invertebrate animal pests will be more sensitive to the compounds (I) than others. Methods of testing a given compound (I) to determine the maximum effective concentration required for killing a specific invertebrate pest are well known; see for example U.S. Pat. Nos. 3,474,170; 3,476,836; and 3,479,029. In general, effective amounts of the compounds (I) for pesticidal activity is obtained when the compounds (I) are applied at concentrations of about 30 to about 6000 ppm, preferably at concentrations of about 100 to about 4000 ppm.

The following example illustrates compositions of the invention (percentages hereafter are w/w unless otherwise specified):

EXAMPLE 45

An emulsifiable concentrate having the following percentage composition:

| | |
|---|---|
| N-methyl-N-[dimethylamino)-thio]-N'-2,4-xylylformamidine | 15.0% |
| Technical alkyl naphthalene boiling at 238° to 293° C. (Velsicol AR50) | 19.7% |
| Xylene | 17.4% |
| Acetone | 17.4% |
| Ethylene dichloride | 25.4% |

-continued

| | |
|---|---|
| Blend of alkyl aryl sulfonates and alkylphenoxy polyethoxy ethanols (Triton X-151) | 5.1% | was prepared by mixing 15.0 lbs. of N-methyl-N-[(dimethylamino)thio]-N'-2,4-xylylformamidine, 19.7 lbs. of Velsicol AR50, 17.4 lbs. of xylene, 17.4 lbs. of acetone, 25.4 lbs. of ethylene dichloride, and 5.1 lbs. of Triton X-151.

6.67 Lbs. of the concentrate mixed with 10 gals. of water gave a spray emulsion containing about 11,000 ppm of active ingredient.

The composition is useful in treating apples for control of mites when applied at a rate of 10 gals. per acre.

EXAMPLE 46

An emulsifiable concentrate having the following percentage composition:

| | |
|---|---|
| N-methyl-N-[(dimethylamino)-thio]-N'-2,4-xylyl-formamidine | 40.0% |
| Technical alkyl napthalene boiling at 238° to 293° C. (Velsicol AR50) | 13.7% |
| Xylene | 12.3% |
| Acetone | 11.3% |
| Ethylene dichloride | 17.7% |
| Blend of alkyl aryl sulfonates and alkylphenoxy polyethoxy ethanol (Triton X-151) | 5.0% | was prepared by mixing 40.0 lbs. of N-methyl-N-[(dimethylamino)thio]-N'-2,4-xylylformamidine, 13.7 lbs. of Velsicol AR50, 12.3 lbs. of xylene, 11.3 lbs. of acetone, 17.7 lbs. of ethylene dichloride, and 5.0 lbs. of Triton X-151.

1.67 Lbs. of the concentrate mixed with 10 gals. of water gave a spray emulsion containing about 8,000 ppm of active ingredient.

The composition is useful in treating citrus for control of mites when applied at a rate of 12 gals. per acre.

EXAMPLE 47

Following the procedure of the preceding Examples 45 and 46, compositions are similarly prepared substituting each of the compounds prepared in Examples 1 through 44, inclusive, for the N-methyl-N-[(dimethylamino)thio]-N'-2,4-xylylformamidine.

I claim:

1. A compound of the formula:

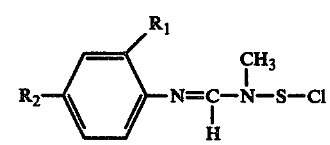

wherein $R_1$ is lower alkyl of from 1 to 4 carbon atoms; and $R_2$ is hydrogen, halogen, or lower alkyl of from 1 to 4 carbon atoms.

* * * * *